(12) United States Patent
Ryan et al.

(10) Patent No.: US 8,383,854 B2
(45) Date of Patent: Feb. 26, 2013

(54) USE OF CHEMICAL REACTION TO SEPARATE ETHYLENE FROM ETHANE IN ETHANE-BASED PROCESSES TO PRODUCE ACETIC ACID

(75) Inventors: Debra Ann Ryan, Keller, TX (US); James A. Foster, Richmond, VA (US)

(73) Assignee: Celanese International Corp., Irving, TX (US)

( * ) Notice: Subject to any disclaimer, the term of this patent is extended or adjusted under 35 U.S.C. 154(b) by 569 days.

(21) Appl. No.: 12/223,222

(22) PCT Filed: Jan. 30, 2007

(86) PCT No.: PCT/US2007/002350
§ 371 (c)(1),
(2), (4) Date: Aug. 30, 2010

(87) PCT Pub. No.: WO2007/092189
PCT Pub. Date: Aug. 16, 2007

(65) Prior Publication Data
US 2011/0009667 A1    Jan. 13, 2011

Related U.S. Application Data

(60) Provisional application No. 60/765,983, filed on Feb. 7, 2006.

(51) Int. Cl.
*C07C 51/16* (2006.01)
(52) U.S. Cl. .................................................. 562/548
(58) Field of Classification Search .................. 562/548
See application file for complete search history.

(56) References Cited

U.S. PATENT DOCUMENTS

| | | | |
|---|---|---|---|
| 6,399,816 B1 | 6/2002 | Borchert et al. | 562/512.2 |
| RE39,074 E * | 4/2006 | Borchert et al. | 562/548 |
| 2002/0082445 A1* | 6/2002 | Ellis et al. | 560/241.1 |

* cited by examiner

*Primary Examiner* — Taylor Victor Oh
(74) *Attorney, Agent, or Firm* — Michael W. Ferrell

(57) ABSTRACT

Described herein is a process in which acetic acid is produced by ethane oxidation. One byproduct of the ethane oxidation is ethylene. High ethylene content in the recycle gas stream will lead to poor efficiencies and higher losses to the COx byproduct in the acetic acid reactor. In fact, ethylene in the recycle feed competes with the ethane for the limited amount of oxygen feed, resulting in higher inefficiencies to carbon oxides than straight ethane oxidation. Ethylene is removed in this process by a further oxidation reaction at a temperature low enough such that ethane is not reactive, but the ethylene is converted to acetic acid. Either the ethane oxidation reactor effluent or a portion or all of the recycle stream to the ethane oxidation reactor, or any combination of the same, can be processed in this manner to reduce the ethylene content of those streams.

23 Claims, 4 Drawing Sheets

USE OF CHEMICAL REACTION TO SEPARATE ETHYLENE FROM ETHANE IN ETHANE-BASED PROCESSES TO PRODUCE ACETIC ACID

FIELD OF THE INVENTION

This invention relates to the process of oxidizing ethane to produce acetic acid. In particular, this invention relates to a method of oxidizing ethane to acetic acid wherein ethylene is removed from an ethane/ethylene recycle stream using a chemical reaction.

BACKGROUND OF THE INVENTION

The oxidative dehydrogenation of ethane to acetic acid in the gas phase is well known in the art. Generally, this process involves reacting a gaseous feed in a fluidized bed or in a fixed-bed reactor. The gaseous feed comprises ethane and/or ethylene which are fed to the reactor as pure gases or in admixture with one or more other gases. Examples of such additional, or carrier, gases are nitrogen, methane, carbon monoxide, carbon dioxide, air and/or water vapor. The gas comprising molecular oxygen can be air or a gas comprising more or less molecular oxygen than air, e.g. oxygen. Relatively high oxygen contents are preferred since the achievable ethane conversion, and thus the yield of acetic acid, is higher. Oxygen or the gas comprising molecular oxygen is preferably added in a concentration range outside the explosive limits under the reaction conditions since this makes the process easier to carry out. However, it is also possible to employ an ethane/ethylene to oxygen ratio within the explosive limits. The reaction is carried out at temperatures of from 400 to 600° C., while the pressure can be atmospheric or superatmospheric, e.g. in the range from 1 to 50 bar.

Ethane is usually first mixed with the inert gases such as nitrogen or water vapor before oxygen or the gas comprising molecular oxygen is fed in. The mixed gases are preferably preheated to the reaction temperature in a preheating zone before the gas mixture is brought into contact with the catalyst. Acetic acid is separated from the gas leaving the reactor by condensation. The remaining gases are recirculated to the reactor inlet where oxygen or the gas comprising molecular oxygen and also ethane and/or ethylene are metered in. The recirculated gases will always comprise both ethylene and ethane.

FIG. 1 shows a common prior art acetic acid production process. In this basic system, an ethane containing stream (1) is fed along with an oxygen containing gas (2) into an ethane oxidation reactor (3). This reactor can be either a fluidized bed or a fixed-bed reactor. Inside the reactor (3), ethane is oxidized into acetic acid, ethylene, and various carbon oxides ($CO_x$). The gaseous reactor effluent (4) that contains these three primary components is fed into a recycle gas scrubber (5), which produces a top stream containing ethylene, ethane, and $CO_x$. The top stream (7) from the recycle gas scrubber is routed to a processing step (8) that removes the $CO_x$ from the top stream. The purified stream (9) is then recycled to the oxidation reactor (3) for further conversion into acetic acid. The bottom stream (6) from the recycle gas scrubber (5), which contains acetic acid, water, and heavy ends by-products, may be purified as known in the art to provide purified acetic acid. For example, the bottom stream may be routed to a drying column to remove water followed by a heavy ends column to remove propionic acid and other heavy components.

High Ethylene content in the recirculated gas stream will lead to poor efficiencies and higher losses to the COx byproduct in the acetic acid reactor. In fact, ethylene in the recycle feed competes with the ethane for the limited amount of oxygen feed, resulting in higher inefficiencies to carbon oxides than straight ethane oxidation. It is therefore desirable to develop a process where there is no ethylene in the recycle stream to the ethane oxidation reactor.

SUMMARY OF THE INVENTION

It is an object of this invention to provide a process in which acetic acid is produced by ethane oxidation. One byproduct of the ethane oxidation, ethylene, is removed by further a further reaction at a temperature low enough such that ethane is not reactive, but the ethylene is converted to acetic acid. Either the ethane oxidation reactor effluent or the recycle stream to the ethane oxidation reactor, or both, can be processed in this manner to reduce the ethylene content of those streams.

DETAILED DESCRIPTION OF THE INVENTION

Figure 1:
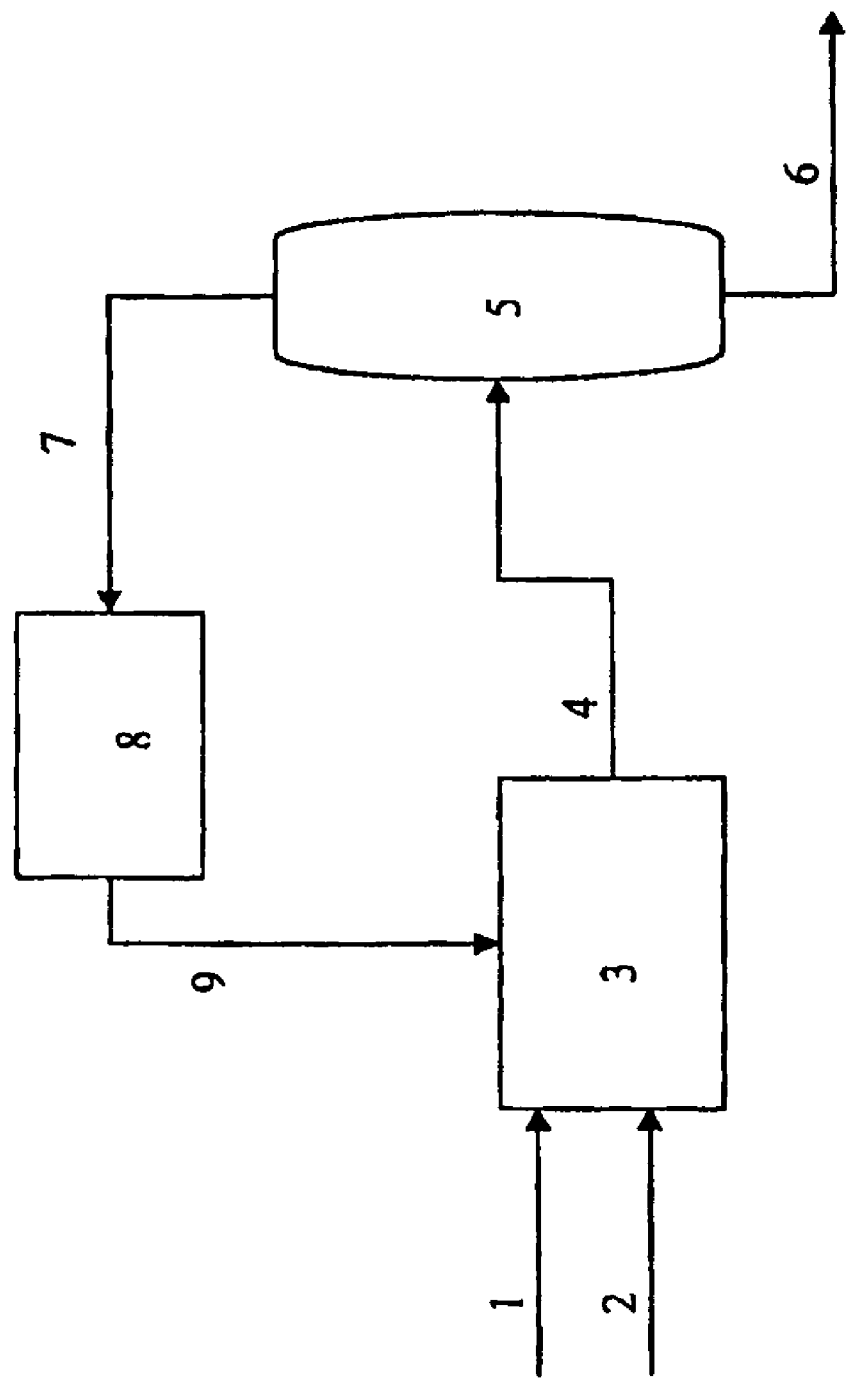
FIG. 1 shows a prior art acetic acid production process.

The present invention provides a process for selectively preparing acetic acid from the oxidation of ethane. One byproduct of the ethane oxidation reaction is ethylene. It is an objective of this application to remove as much produced ethylene from the system so as to improve the overall efficiencies of the entire acetic acid production process.

The oxidation of ethane can be carried out in a fluidized bed or in a fixed bed reactor. For use in a fluidized bed, the catalyst is normally ground to a particle size in the range from 10 to 200 μm or prepared by spray drying.

The gaseous feedstock, and any recycle gas combined with said feedstock gas, contains primarily ethane, but may contain some amount of ethylene, and is fed to the reactor as a pure gas or in a mixture with one or more other gases. Suitable examples of such additional or carrier gases are nitrogen, methane, carbon monoxide, carbon dioxide, air and/or steam. The gas containing molecular oxygen may be air or a gas which has a higher or lower molecular oxygen concentration than air, for example pure oxygen. The ethane oxidation reaction is generally carried out at about 400 to about 600° C., preferably about 450 to about 550° C., the key being that the temperature be high enough to oxidize ethane. The appropriate temperature will depend upon the catalyst used in the ethane oxidation reactor. There are a wide range of catalysts for use in this reaction, and one of ordinary skill in the art will know how to optimize catalyst performance by finding the appropriate reaction temperature. The pressure can be atmospheric or superatmospheric, for example about 1 to about 50 bar, preferably about 1 to about 30 bar.

The oxidation reaction produces a mixture of gases including ethylene, acetic acid, water, $CO_x$ (CO and $CO_2$), unreacted ethane, and assorted heavy by-products. The product gas effluent from the reactor is preferably filtered to remove catalyst fines and is then routed to a recycle gas scrubber, which produces a top stream containing ethylene, ethane, and $CO_x$. The top stream from the recycle gas scrubber is routed to a fixed bed CO converter followed by a processing step that removes the $CO_x$ from the top stream. The bottom stream from the recycle gas scrubber, which contains acetic acid, water, and heavy ends by-products, may be purified as known in the art to provide purified acetic acid. For example, the bottom stream may be routed to a drying column to remove water followed by a heavy ends column to remove propionic acid and other heavy components.

In accordance with certain teachings of the present invention, ethylene is removed from the oxidation reaction product by means of a chemical reaction. This reaction can take place at any point in the process, for example immediately after the ethane oxidation reactor or in the recycle gas line. To accomplish this reaction, the stream is passed over an oxidation catalyst at a temperature low enough to convert ethylene to acetic acid, but not convert ethane in the stream to acetic acid. In one embodiment, this step is carried out by passing the stream through a fixed-bed or fluidized bed reactor containing the same catalyst used in the ethane oxidation step, however in another embodiment the catalysts can be different. Most catalysts that are capable of oxidizing ethane to acetic acid at higher temperatures are capable of oxidizing ethylene to acetic acid at lower temperatures. As high ethylene content in the recycle gas stream will lead to poor efficiencies and higher losses to the COx byproduct in the acetic acid reactor, the removal of ethylene from the process, via its conversion to acetic acid, will increase the efficiency of the process and the overall acetic acid production.

One of skill in the art will appreciate that the towers, scrubbers, and routing referred to in the preceding paragraphs will have associated with them various heat exchangers, pumps, and connectors and will have operating parameters that are determined by the particular mixture of gases involved. It is within the ability of one of ordinary skill in the art to determine the proper configurations and parameters, given the present disclosure.

In a preferred embodiment, the oxidation catalyst used for both the ethane oxidation reaction and the ethylene removal reaction has the formula $Mo_1V_{0.55}Nb_{0.09}Sb_{0.01}Ca_{0.01}Pd_{0.00075}$. One of skill in the art will appreciate that the catalyst is actually a mixed oxide having the formula $Mo_1V_{0.55}Nb_{0.09}Sb_{0.01}Ca_{0.01}Pd_{0.00075}O_z$. The amount of oxygen, z, is determined by the oxidation states of Mo, V, Nb, Sb, Ca and Pd and cannot be generally specified.

The catalyst of the invention can be prepared, for example, as described in U.S. Pat. No. 6,399,816, by Borchert, et al., the entire contents of which are incorporated herein by reference. Briefly, metal compounds that are the sources of the metals in the catalyst are combined in at least one solvent in appropriate amounts to form a solution. These start from a slurry, in particular an aqueous solution, comprising the individual starting components of the elements in the appropriate proportions. The starting materials of the individual components for preparing the catalyst of the invention are, apart from the oxides, preferably water-soluble substances such as ammonium salts, nitrates, sulfates, halides, hydroxides and salts of organic acids which can be converted into the corresponding oxides by heating. To mix the components, aqueous solutions or suspensions of the metal salts are prepared and mixed. In the case of molybdenum, it is advisable to use the corresponding molybdates, e.g. ammonium molybdate, as starting compounds because of their commercial availability. Suitable palladium compounds are, for example, palladium (II) chloride, palladium(II) sulfate, tetramminepalladium(II) nitrate, palladium(II) nitrate and palladium(II) acetylacetonate. Suitable compounds for each element are known in the art.

Suitable solvents include water, alcohols (including but not limited to methanol, ethanol, propanol, and diols etc.) as well as other polar solvents known in the art. Generally, water is preferred. The water is any water suitable for use in chemical synthesis including, without limitation, distilled water and deionized water. The amount of water present is that amount sufficient to keep the elements substantially in solution long enough to avoid or minimize compositional and/or phase segregation during the preparation steps. Once the aqueous solution is formed, the water is removed by a combination of any suitable methods known in the art to form a catalyst precursor. Such methods include, without limitation, vacuum drying, freeze drying, spray drying, rotary evaporation, and air drying. Rotary evaporation or air drying are generally preferred.

Once obtained, the catalyst precursor can be calcined under an inert atmosphere. The inert atmosphere may be any material which is substantially inert to, i.e., does not react or interact with, the catalyst precursor. Suitable examples include, without limitation, nitrogen, argon, xenon, helium or mixtures thereof. Preferably, the inert atmosphere is argon or nitrogen, more preferably argon. The inert atmosphere may or may not flow over the surface of the catalyst precursor. Typically, if nitrogen is used, flowing is used. If the inert atmosphere is argon, then typically flowing is not used. When the inert atmosphere does flow over the surface of the catalyst precursor, the flow rate can vary over a wide range, for example, at a space velocity from 1 to 500 $hr^{-1}$. The calcination is typically done at a temperature of from 350° C. to 850° C., preferably from 400° C. to 700° C., more preferably from 500° C. to 640° C. The calcination is performed for long enough to form the catalyst. In one embodiment, the calcination is performed from 0.5 to 30 hours, preferably from 1 to 25 hours and more preferably from 1 to 15 hours.

The catalyst of the invention may be used as a solid catalyst alone or may be used with a suitable support. Conventional support materials are suitable, for example, porous silicon dioxide, ignited silicon dioxide, kieselguhr, silica gel, porous or nonporous aluminum oxide, titanium dioxide, zirconium dioxide, thorium dioxide, lanthanum oxide, magnesium oxide, calcium oxide, barium oxide, tin oxide, cerium dioxide, zinc oxide, boron oxide, boron nitride, boron carbide, boron phosphate, zirconium phosphate, aluminum silicate, silicon nitride or silicon carbide, but also glass, carbon-fiber, carbon, activated carbon, metal-oxide or metal networks or corresponding monoliths.

Support materials should be chosen based on optimizing both the surface area and pore size for the specific oxidation of interest. The catalyst can be employed after shaping as a regularly or irregularly shaped support element, but also in powder form as a heterogeneous oxidation catalyst.

Alternatively, the catalyst may be encapsulated in a material. Suitable materials for encapsulation include $SiO_2$, $P_2O_5$, MgO, $Cr_2O_3$, $TiO_2$, $ZrO_2$, and $Al_2O_3$. Methods of encapsulating materials in oxides are known in the art. A suitable method of encapsulating materials in oxides is described in U.S. Pat. No. 4,677,084 and references cited therein, the entire contents of which are incorporated herein by references.

Figure 2:
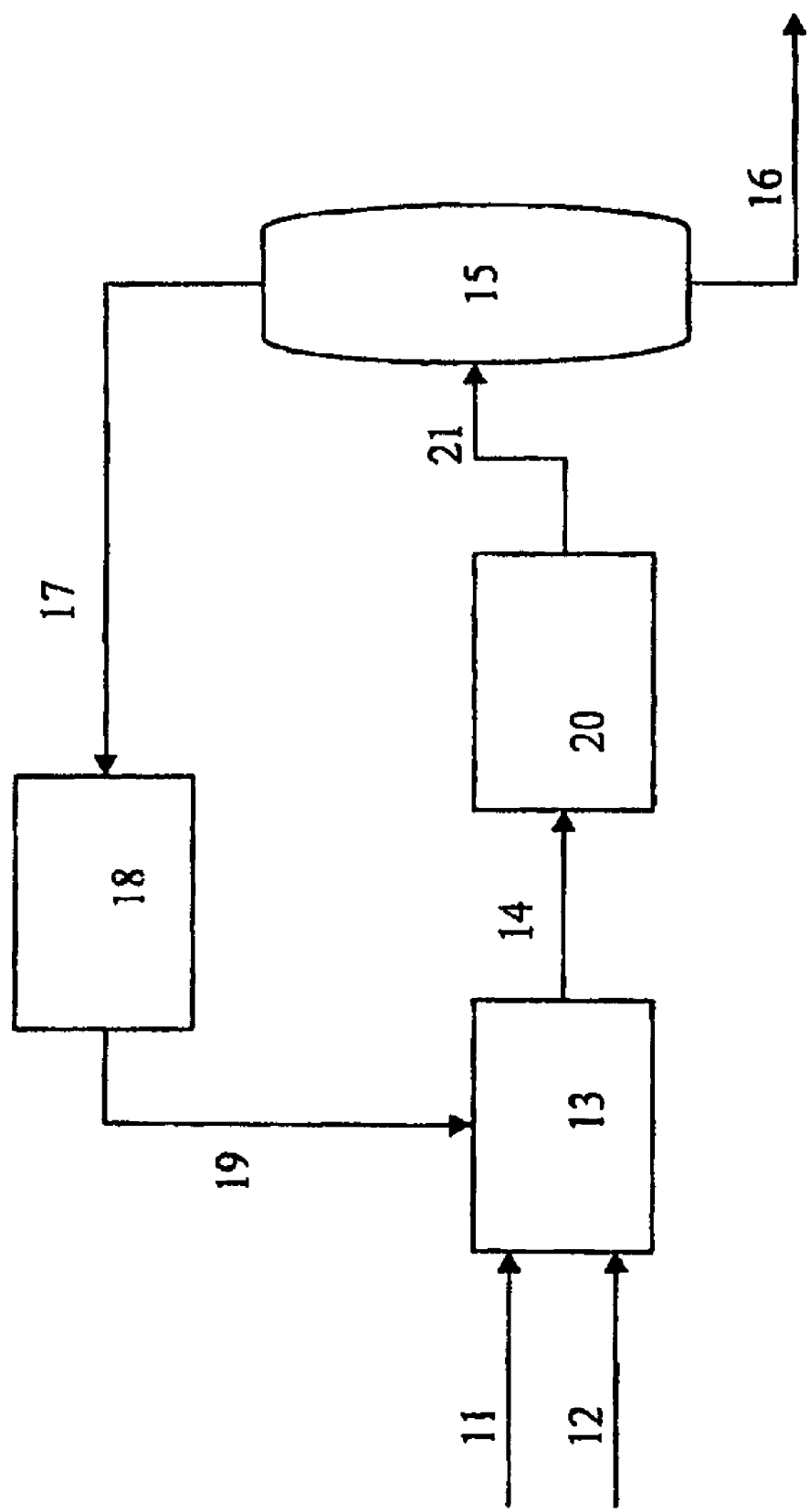
FIG. 2 shows one embodiment of the acetic acid production process of the present invention.

FIG. 2 shows one embodiment of the present invention. In this embodiment, the gaseous ethane feedstock (11) and any recycle gas (19) are fed to the ethane oxidation reactor (13) as a pure gas or in a mixture with one or more carrier gases described above. An oxygen containing gas (12), preferably pure oxygen, is also fed to the reactor (13). The ethane oxidation reaction temperature is generally carried out at about 400 to about 600° C., preferably about 450 to about 550° C., depending on the catalyst used, the key being that the temperature be high enough to oxidize ethane. The appropriate temperature will depend upon the catalyst used in the ethane oxidation reactor, however in one embodiment the catalyst has a formula $Mo_1V_{0.55}Nb_{0.09}Sb_{0.01}Ca_{0.01}Pd_{0.0075}$.

The oxidation reaction produces a mixture of gases (14) that includes ethylene, acetic acid, water, $CO_x$, unreacted ethane, and assorted heavy by-products. The ethane oxidation product gas (14) is then passed through a second oxidation reactor (20) where at least some ethylene is oxidized into acetic acid. The ethylene oxidation reaction temperature is generally carried out at about 150 to about 250° C., preferably about 200 to about 250° C., depending on the catalyst used, the key being that the temperature be high enough to oxidize ethylene, but low enough that substantially no further ethane is oxidized. This allows for the removal of ethylene from the stream, and also increases acetic acid production. The appropriate temperature will depend upon the catalyst used in the ethane oxidation reactor, however in one embodiment the catalyst for the ethylene oxidation is the same used for the ethane oxidation. In a further embodiment, the formula of that catalyst is $Mo_1V_{0.55}Nb_{0.09}Sb_{0.01}Ca_{0.01}Pd_{0.00075}$.

The gaseous product stream (21) of the second oxidation reactor (20) still includes water, $CO_x$, unreacted ethane, and assorted heavy by-products, but also contains substantially less ethylene and more acetic acid than the ethane oxidation reactor product stream (14). The product gas effluent from the reactor is preferably filtered to remove catalyst fines (not shown) and is then routed to a recycle gas scrubber (15), which produces a top stream (17) containing ethylene, ethane, and $CO_x$. The top stream from the recycle gas scrubber is routed to a fixed bed CO converter followed by a processing step that removes the $CO_x$ from the top stream (18), and is then recycled as stream (19) back to the ethylene oxidation reactor (13). The bottom stream (16) from the recycle gas scrubber, which contains acetic acid, water, and heavy ends by-products, may be purified as known in the art to provide purified acetic acid.

Figure 3:
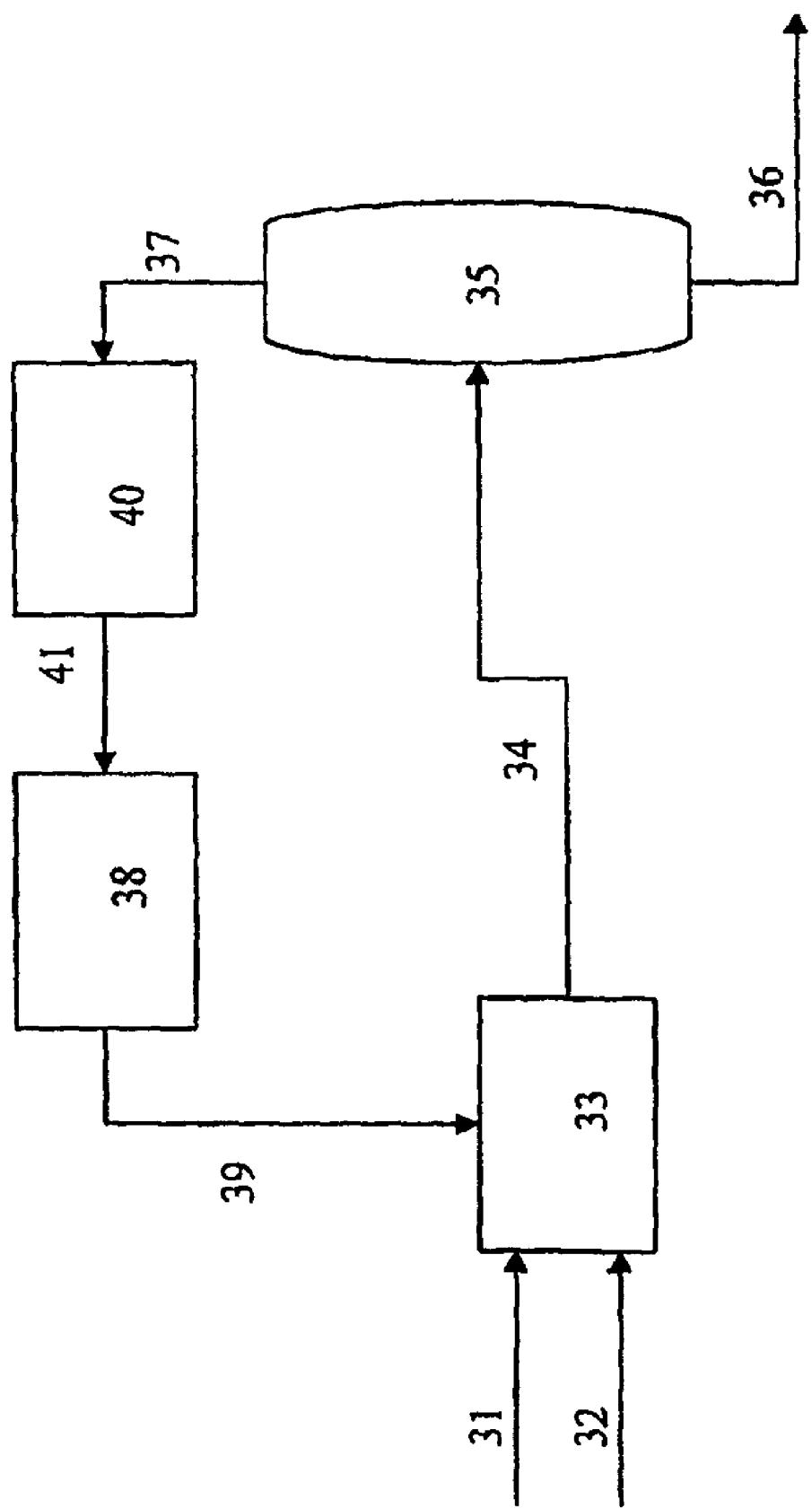
FIG. 3 shows a second embodiment of the acetic acid production process of the present invention.

A further embodiment is shown below in FIG. 3. In this embodiment, the gaseous ethane feedstock (31) and any recycle gas (39) are fed to the ethane oxidation reactor (33) as a pure gas or in a mixture with one or more carrier gases described above. An oxygen containing gas (32), preferably pure oxygen, is also fed to the reactor (33). The ethane oxidation reaction temperature is generally carried out at about 400 to about 600° C., preferably about 450 to about 550° C., depending on the catalyst used, the key being that the temperature be high enough to oxidize ethane. The appropriate temperature will depend upon the catalyst used in the ethane oxidation reactor, however in one embodiment the catalyst has a formula $Mo_1V_{0.05}Nb_{0.09}Sb_{0.01}Ca_{0.01}Pd_{0.00075}$.

The oxidation reaction produces a mixture of gases (34) that includes ethylene, acetic acid, water, $CO_x$, unreacted ethane, and assorted heavy by-products. The product gas effluent from the reactor is preferably filtered to remove catalyst fines (not shown) and is then routed to a recycle gas scrubber (35), which produces a top stream (37) containing ethylene, ethane, and $CO_x$. The bottom stream (36) from the recycle gas scrubber, which contains acetic acid, water, and heavy ends by-products, may be purified as known in the art to provide purified acetic acid.

The top stream (37) from the recycle gas scrubber (35) is then passed through a second oxidation reactor (40) where at least some ethylene is oxidized into acetic acid. The ethylene oxidation reaction temperature is generally carried out at about 150 to about 250° C., preferably about 200 to about 250° C., depending on the catalyst used, the key being that the temperature be high enough to oxidize ethylene, but low enough that substantially no further recycle ethane is oxidized. The gaseous product stream (41) of the second oxidation reactor (40) still includes $CO_x$, and unreacted ethane. Finally, the ethylene oxidation reactor product (41) is routed to a fixed bed CO converter followed by a processing step that removes the $CO_x$ from the top stream (38), and is then recycled as stream (39) back to the ethylene oxidation reactor (33).

Figure 4:
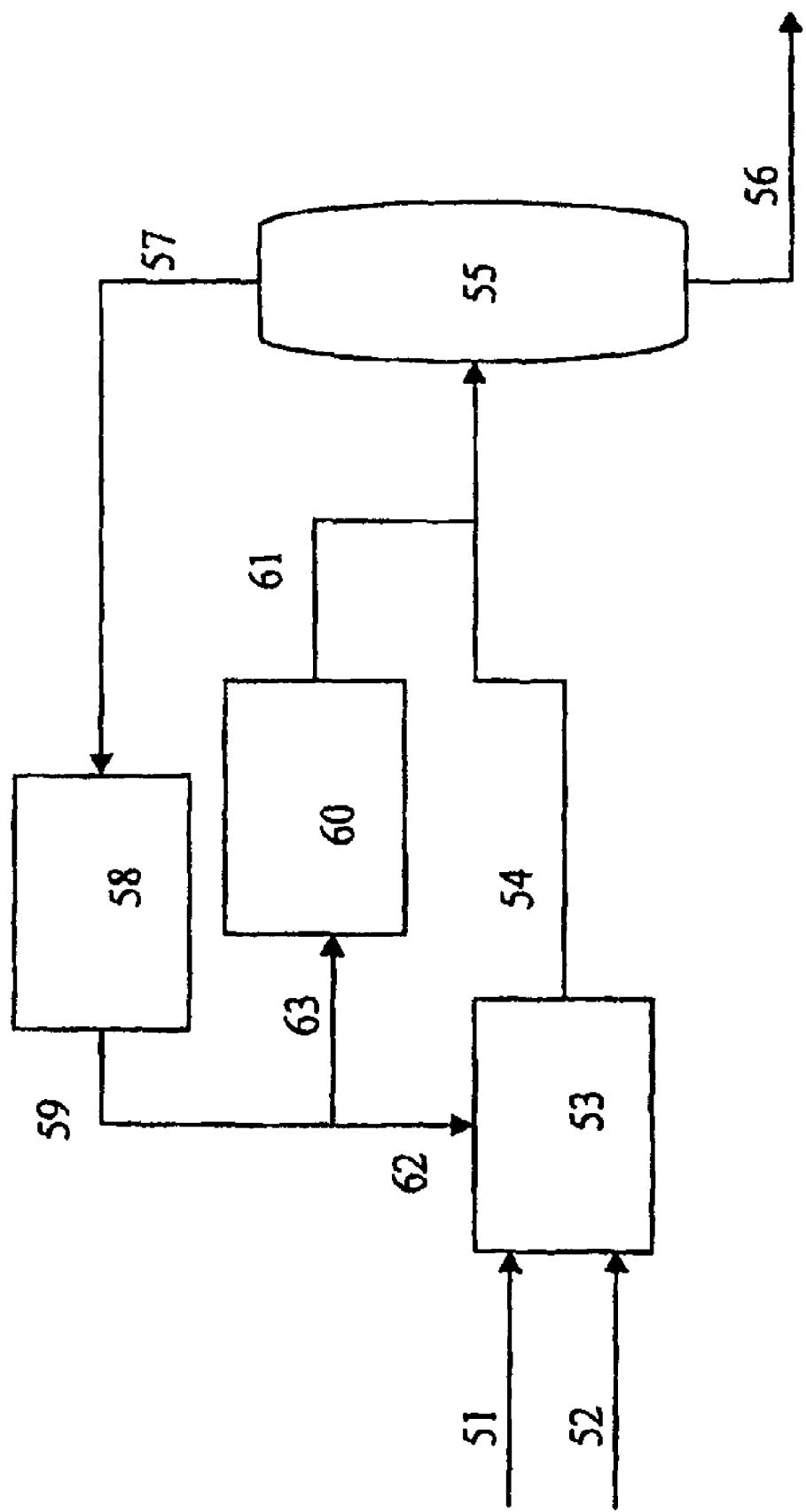
FIG. 4 shows a third embodiment of the acetic acid production process of the present invention.

A further embodiment is shown below in FIG. 4. In this embodiment, the gaseous ethane feedstock (51) and any recycle gas (62) are fed to the ethane oxidation reactor (53) as a pure gas or in a mixture with one or more carrier gases described above. An oxygen containing gas (52) preferably pure oxygen, is also fed to the reactor (53). The oxidation reaction produces a mixture of gases (54) that includes ethylene, acetic acid, water, $CO_x$, unreacted ethane, and assorted heavy by-products. The product gas effluent (54) from the reactor (53) is combined with the reactor effluent (61) from the ethylene oxidation reactor (60), filtered to remove catalyst fines (not shown) and is then routed to a recycle gas scrubber (55), which produces a top stream (57) containing ethylene, ethane, and $CO_x$. The bottom stream (56) from the recycle gas scrubber, which contains acetic acid, water, and heavy ends by-products, may be purified as known in the art to provide purified acetic acid.

The top stream (57) from the recycle gas scrubber (55) is routed to a fixed bed CO converter followed by a processing step that removes the $CO_x$ from the top stream (58). The resultant gas (59) is then split into two streams, a first stream (62) that is recycled back to the ethylene oxidation reactor (53), and a second stream (63) that is sent to ethylene oxidation reactor (60). The ethylene oxidation reaction temperature is generally carried out at about 150 to about 250° C., preferably about 200 to about 250° C., depending on the catalyst used, the key being that the temperature be high enough to oxidize at least some ethylene, but low enough that substantially no ethane is oxidized. The gaseous product stream (61) of the second oxidation reactor (61) includes acetic acid, $CO_x$, and unreacted ethane. It is combined with the product gas effluent (54) from the reactor (53) and is then routed to a recycle gas scrubber (55) as described hereinabove.

The preceding description is set forth for purposes of illustration only and is not to be taken in a limited sense. Various modifications and alterations will be readily apparent to persons skilled in the art. It is intended, therefore, that the foregoing be considered as exemplary only and that the scope of the invention be ascertained from the following claims.

The invention claimed is:

1. A process for the production of acetic acid, comprising: oxidizing ethane in a first reactor at a first temperature to produce a first effluent stream comprising acetic acid and ethylene; and oxidizing the first effluent stream in a second reactor at a second temperature lower than said first temperature and low enough to selectively oxidize ethylene to acetic acid to thereby remove ethylene from the first effluent stream and increase the acetic acid content of the first effluent stream.

2. The process of claim 1, wherein the first temperature of the first reactor is from about 400° C. to about 600° C.

3. The process of claim 1, wherein oxidizing the first effluent stream in the second reactor at the second temperature occurs at from about 150° C. to about 250° C.

4. The process of claim 1, wherein oxidizing ethane and oxidizing the first effluent stream is performed with a catalyst having the chemical formula $Mo_1V_{0.55}Nb_{0.09}Sb_{0.01}Ca_{0.01}Pd_{0.00075}$.

5. The process of claim 1, wherein oxidizing ethane is performed using a fixed bed reactor or a fluidized bed reactor.

6. The process of claim 1, wherein oxidizing the first effluent stream is performed using a fixed bed or a fluidized bed reactor.

7. The process of claim 1, further comprising using a carrier gas for oxidizing ethane or oxidizing ethylene and the carrier gas is selected from the group consisting of nitrogen, methane, carbon monoxide, carbon dioxide, air, steam and combinations thereof.

8. The process of claim 1, wherein a solvent is used for oxidizing ethane or oxidizing ethylene and the solvent is selected from the group consisting of methanol, ethanol, propanol, diols, water, distilled water, and deionized water, and combinations thereof.

9. A process for the production of acetic acid, comprising: oxidizing ethane in a first reactor at a first temperature to produce a first effluent stream comprising acetic acid and ethylene; oxidizing the first effluent stream in a second reactor at a second temperature lower than said first temperature and low enough to selectively oxidize ethylene to acetic acid to thereby remove ethylene from the first effluent stream and produce a second effluent stream enriched in acetic acid as compared with the first effluent stream; and flowing the second effluent stream through a recycle gas scrubber to produce an acetic acid stream and a recycle stream.

10. The process of claim 9, further comprising flowing the second effluent stream through a filter before it flows through the recycle gas scrubber.

11. The process of claim 9, further comprising a flowing the recycle stream through a $CO_x$ scrubber.

12. The process of claim 9, wherein the first reactor is a fixed bed or fluidized bed reactor.

13. The process of claim 9, wherein the second reactor is a fixed bed or a fluidized bed reactor.

14. The process of claim 9, wherein the first temperature of the first reactor is from about 400° C. to about 600° C. and the second temperature of the second reactor is from about 150° C. to about 250° C.

15. A process for the production of acetic acid, comprising: oxidizing ethane in a first reactor at a first temperature to produce a first effluent stream comprising acetic acid and ethylene; flowing the first effluent stream through a recycle gas scrubber to produce an acetic acid stream and a recycle stream; and oxidizing the recycle stream in a second reactor at a second temperature lower than said first temperature and low enough to selectively oxidize ethylene to acetic acid to thereby remove ethylene from the recycle stream and produce a second effluent stream enriched in acetic acid as compared with the recycle stream.

16. The process of claim 15, further comprising flowing the first effluent stream through a filter before the first effluent stream flows into the recycle gas scrubber.

17. The process of claim 15, further comprising a $CO_x$ scrubber in the recycle stream.

18. The process of claim 15, wherein the first temperature of the first reactor is from about 400° C. to about 600° C. and the second temperature of the second reactor from about 150° C. to about 250° C.

19. A process for the production of acetic acid, comprising: oxidizing ethane in a first reactor to produce a first effluent stream comprising acetic acid and ethylene; flowing the first effluent stream through a recycle gas scrubber to produce an acetic acid stream and a recycle stream; flowing a portion of the recycle stream to the first reactor; and oxidizing a second portion of the recycle stream in a second reactor at a temperature low enough to selectively oxidize ethylene to acetic acid to produce a second effluent stream, wherein the second effluent stream and first effluent stream are combined before the first effluent stream flows through the recycle gas scrubber.

20. The process of claim 1, wherein the second temperature of the second reactor is low enough such that substantially no ethane present is oxidized in the second reactor.

21. The process of claim 9, wherein the second temperature of the second reactor is low enough such that substantially no ethane present is oxidized in the second reactor.

22. The process of claim 15, wherein the second temperature of the second reactor is low enough such that substantially no ethane present is oxidized in the second reactor.

23. The process of claim 19, wherein the second temperature of the second reactor is low enough such that substantially no ethane present is oxidized in the second reactor.

* * * * *